(12) United States Patent
Borak et al.

(10) Patent No.: US 11,311,422 B1
(45) Date of Patent: Apr. 26, 2022

(54) COMPRESSION GARMENT

(71) Applicants: George O. Borak, Clearwater, FL (US); Justice Anderson, Clearwater, FL (US)

(72) Inventors: George O. Borak, Clearwater, FL (US); Justice Anderson, Clearwater, FL (US)

(73) Assignee: Amerx Health Care Corp., Oldsmar, FL (US)

( * ) Notice: Subject to any disclaimer, the term of this patent is extended or adjusted under 35 U.S.C. 154(b) by 174 days.

(21) Appl. No.: 15/653,629

(22) Filed: Jul. 19, 2017

Related U.S. Application Data

(60) Provisional application No. 62/395,611, filed on Sep. 16, 2016.

(51) Int. Cl.
*A61F 13/08* (2006.01)
*A41D 13/05* (2006.01)

(52) U.S. Cl.
CPC ........ *A61F 13/085* (2013.01); *A41D 13/0556* (2013.01); *A41D 13/0562* (2013.01)

(58) Field of Classification Search
CPC ...... A61F 13/085; A61F 13/08; A61F 13/108; A61F 13/06; A61F 13/102; A61F 2013/0028; A61F 13/062; A61F 5/02; A61F 5/022; A61F 5/024; A61F 5/026; A61F 5/028; A61F 5/0104; A61F 5/0106; A61F 5/0109; A61F 5/0118; A61F 5/0123; A61F 5/013; A61F 2005/0165; A61F 2005/0167; A41D 17/00; A41D 17/005; A41D 17/02; A41D 13/0543; A41D 13/0556; A41D 13/0562; A41D 2300/30; A41D 2300/32; A41D 2300/322; A41D 2300/33; A41D 2300/332; A41B 11/08; A41B 11/10; A41B 2300/30; A41B 2300/32; A41B 2300/322; A41B 2300/33; A41B 2300/332; A41B 11/12; A43C 7/00; A43C 11/008; A43C 1/003; A43C 1/00; A43C 1/006;

(Continued)

(56) References Cited

U.S. PATENT DOCUMENTS 1,380,883 A * 6/1921 Samuelh .................. A61F 5/03
450/119
1,499,805 A * 7/1924 Chatterton ............ A61F 13/085
36/2 R (Continued)

FOREIGN PATENT DOCUMENTS

WO WO-9310727 A1 * 6/1993 ........... A61F 5/0104

*Primary Examiner* — Amy Vanatta
(74) *Attorney, Agent, or Firm* — Lewellyn Law, PLLC; Stephen Lewellyn

(57) ABSTRACT

A first section encompasses an extremity of a wearer. The compression garment has a front, a back, a left side, a right side, a top, a bottom, an interior, and an exterior. A primary fastener separably couples and uncouples an opening in the garment. An adjustment assembly has a left tensioner with secondary fasteners and a right tensioner with secondary fasteners. A plurality of left apertures are adjacent to the left tensioner. A plurality of right apertures are adjacent to the right tensioner. Each of a plurality of cords has a left end coupled to the left tensioner and a right end coupled to an associated right tensioner. Each of the plurality of cords passes through associated left and right apertures.

6 Claims, 6 Drawing Sheets

(58) Field of Classification Search
CPC ... A43C 1/02; A43C 11/00; A41F 1/00; A41F 1/008; A41F 1/04; A41F 13/00
USPC .................................. 2/61, 242, 239; 36/2 R
See application file for complete search history.

(56) References Cited

U.S. PATENT DOCUMENTS

| | | | | |
|---|---|---|---|---|
| 1,798,471 | A * | 3/1931 | Janke | A43B 3/02 |
| | | | | 450/153 |
| 1,974,283 | A * | 9/1934 | Kendrick | A61F 5/03 |
| | | | | 128/95.1 |
| 2,100,964 | A * | 11/1937 | Kendrick | A61F 5/028 |
| | | | | 450/119 |
| 2,280,025 | A * | 4/1942 | Bollinger | A61F 13/085 |
| | | | | 36/2 R |
| 2,694,395 | A * | 11/1954 | Brown | A61F 5/012 |
| | | | | 128/118.1 |
| 2,747,570 | A * | 5/1956 | Jobst | A61H 9/0078 |
| | | | | 601/149 |
| 2,793,368 | A * | 5/1957 | Nouel | A41C 1/00 |
| | | | | 450/119 |
| 4,508,110 | A * | 4/1985 | Modglin | A61F 5/022 |
| | | | | 2/908 |
| 4,586,272 | A * | 5/1986 | Forster | A41D 17/00 |
| | | | | 36/2 A |
| 5,254,122 | A * | 10/1993 | Shaw | A61F 13/085 |
| | | | | 606/201 |
| 5,769,804 | A * | 6/1998 | Harris | A61F 5/0118 |
| | | | | 602/20 |
| 8,147,438 | B2 * | 4/2012 | Livolsi | A61F 5/0118 |
| | | | | 602/20 |
| 8,469,914 | B2 * | 6/2013 | Allard | A61F 5/0111 |
| | | | | 602/62 |
| 9,387,111 | B2 * | 7/2016 | Klutts | A61F 5/0118 |
| 9,681,991 | B1 * | 6/2017 | Warren | A61F 13/00059 |
| 2014/0188026 | A1 * | 7/2014 | Gaylord | A61F 5/0111 |
| | | | | 602/27 |

* cited by examiner

COMPRESSION GARMENT

CROSS-REFERENCE TO RELATED APPLICATIONS

This application claims the benefit of U.S. Provisional Patent Application Ser. No. 62/395,611, filed Sep. 16, 2016, the entirety of which is incorporated herein by reference.

BACKGROUND OF THE INVENTION

Field of the Invention

The present invention relates to a compression garment, and more particularly, pertains to applying a compressive force or forces to an upper leg and/or a lower leg and/or an ankle and/or a foot and/or an upper arm and/or a lower arm and/or various combinations thereof, of a wearer and for abating an occurrence of, and guarding against a future progression of, edema and phlebitis and thrombosis, the applying and the abating being done in a safe, sanitary, convenient, and economical manner.

Description of the Prior Art

The use of health-related devices is known in the prior art. More specifically, health-related devices previously devised and utilized for the purpose of improving one's health are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, they do not describe a compression garment that allows applying a compressive force to an extremity of a wearer and for abating an occurrence of, and guarding against a future progression of, edema and phlebitis and thrombosis.

In this respect, the compression garment according to the present invention substantially departs from the conventional concepts and designs of the prior art, and in doing so provides an apparatus primarily developed for the purpose of applying a compressive force to a leg and/or foot of a wearer and for abating an occurrence of, and guarding against a future progression of, edema and phlebitis and thrombosis.

Therefore, it can be appreciated that there exists a continuing need for a new and improved compression garment which can be used for applying a compressive force to a leg and/or foot and other extremities of a wearer and for abating an occurrence of, and guarding against a future progression of, edema and phlebitis and thrombosis. In this regard, the present invention substantially fulfills this need.

SUMMARY OF THE INVENTION

In view of the disadvantages inherent in the known types of health-related devices now present in the prior art, the present invention provides an improved compression garment. As such, the general purpose of the present invention, which will be described subsequently in greater detail, is to provide a new and improved compression garment and method which has all the advantages of the prior art and none of the disadvantages.

To attain this, from a broad perspective, the present invention is a compression garment which includes a first section that encompasses an extremity of a wearer. The compression garment has a front, a back, a left side, a right side, a top, and a bottom. The compression garment also has an interior and an exterior. An opening is in the garment. A primary fastener separably couples and uncouples the opening. An adjustment assembly has a left tensioner with secondary fasteners and a right tensioner with secondary fasteners. A plurality of left apertures are adjacent to the left tensioner. A plurality of right apertures are adjacent to the right tensioner. Each of a plurality of cords has a left end coupled to the left tensioner. Each of the plurality of cords has a right end coupled to an associated right tensioner. Each of the plurality of cords passes through associated left and right apertures.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention.

It is important, therefore, that the claims be regarded as including such equivalent constructions insofar as they do not depart from the spirit and scope of the present invention.

It is therefore an object of the present invention to provide a new and improved compression garment which has all of the advantages of the prior art health-related devices and none of the disadvantages.

It is another object of the present invention to provide a new and improved compression garment which may be easily and efficiently manufactured and marketed.

It is a further object of the present invention to provide a new and improved compression garment which is of durable and reliable constructions.

An even further object of the present invention is to provide a new and improved compression garment which is susceptible of a low cost of manufacture with regard to both materials and labor, and which accordingly is then susceptible of low prices of sale to the consuming public, thereby making such compression garment economically available to the buying public.

Lastly, it is an object of the present invention to provide a compression garment for applying a compressive force to an extremity or extremities of a wearer and for abating an occurrence of, and guarding against a future progression of, edema and phlebitis and thrombosis.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
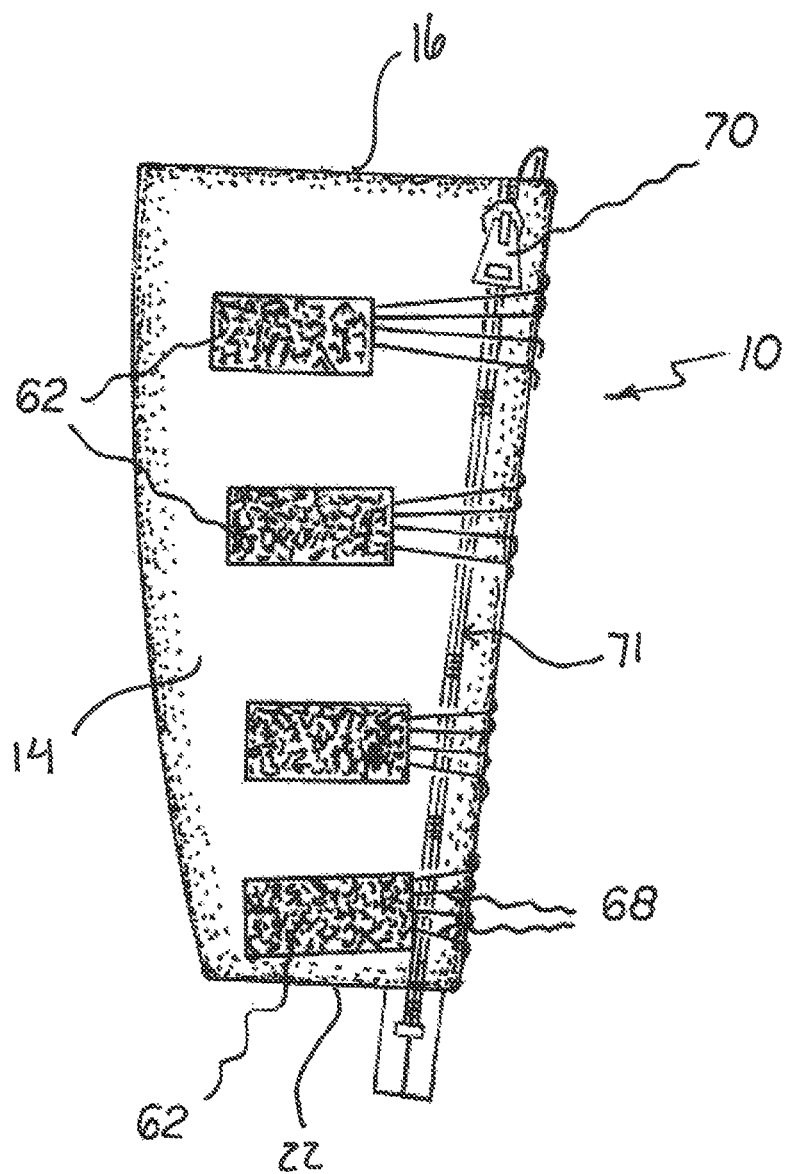
FIG. 1 is a right side elevational view of a compression garment constructed in accordance with the principles of the present invention.
Figure 2:
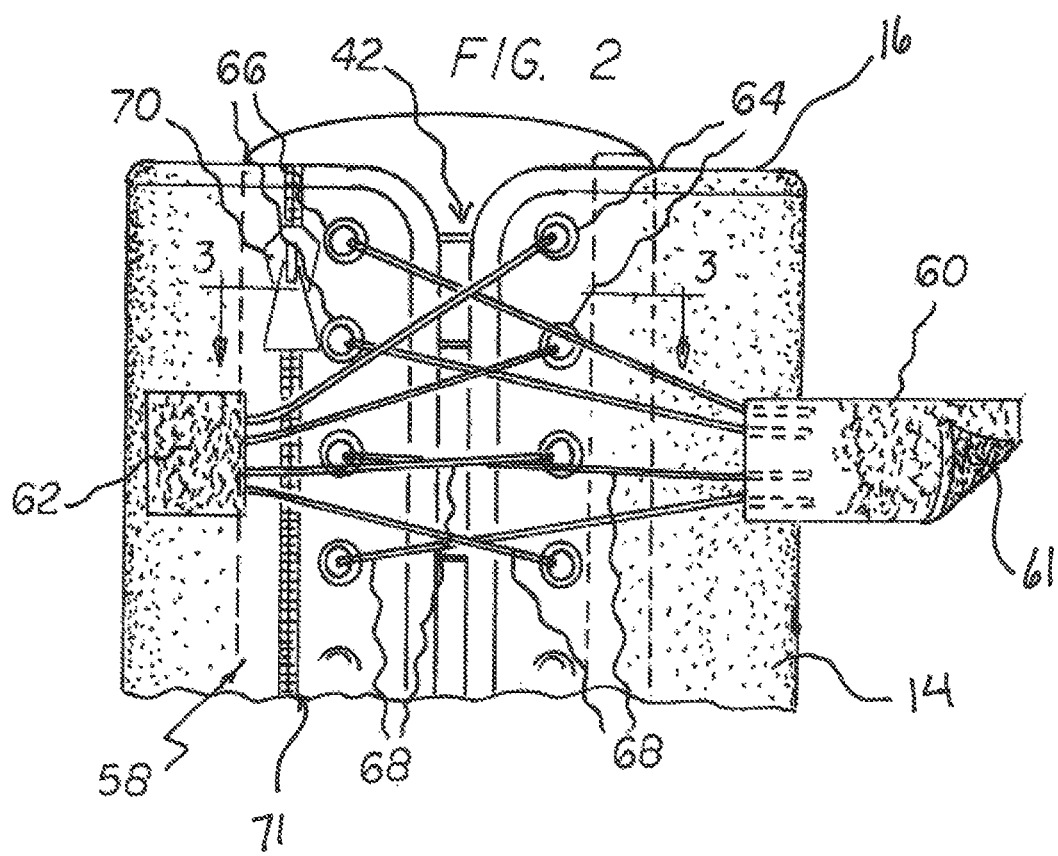
FIG. 2 is an enlarged front elevational view of the upper extent of the compression garment shown in FIG. 1.
Figure 3:
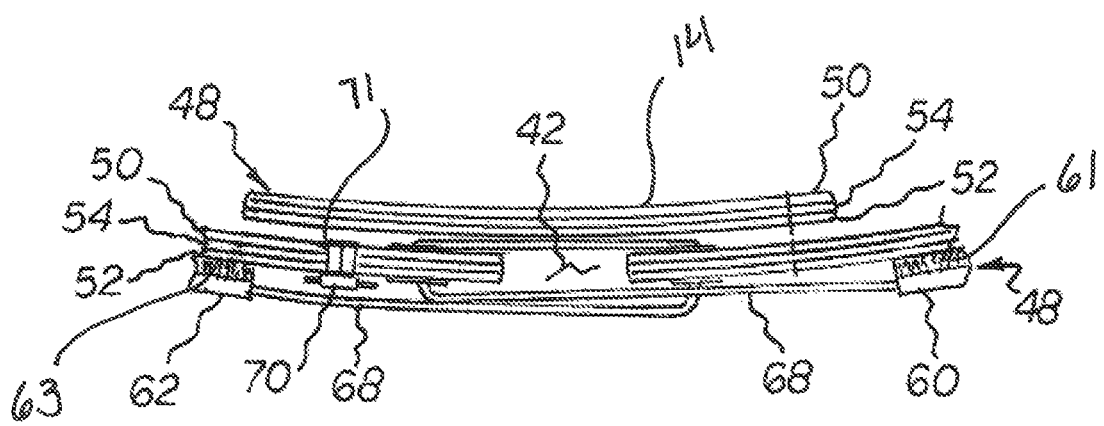
FIG. 3 is a cross-sectional view taken along line 3-3 of FIG. 2.

With reference now to the drawings, and in particular to FIGS. 1-3 thereof, the preferred embodiment of the new and improved compression garment embodying the principles and concepts of the present invention and generally designated by the reference numeral 10 will be described.

The present invention, the compression garment 10 is comprised of a plurality of components. Such components in their broadest context include an opening in the garment. A primary fastener separably couples and uncouples the opening. An adjustment assembly has left and right tensioners with secondary fasteners with secondary fasteners. A plurality of left and right apertures are adjacent to the left and right tensioner. Each of the plurality of cords passes through associated left and right apertures.

From a specific perspective, the invention of the present application is a compression garment 10 for applying a compressive force to an extremity of a wearer, such as an arm and/or a leg and/or a foot and/or an ankle, and for abating an occurrence of, and guarding against a future progression of, edema and phlebitis and thrombosis. The applying and the abating is done in a safe, sanitary, convenient, and economical manner.

The compression garment in the preferred embodiment is designated by reference numeral 10. The compression garment is for applying a compressive force to a lower leg of a wearer and for abating an occurrence of, and guarding against a future progression of, edema and phlebitis and thrombosis. First provided is a first section 14 in a generally frustoconical configuration with a generally vertical axis. The first section encompasses a lower leg of a wearer. The first section 14 has an open bottom 22 and an open top 16.

The first section has a front, a back, a left side, and a right side. The compression garment has an interior and an exterior.

A front opening 42 is provided in the front extending from the open top 16 to a location adjacent to the open bottom. The adjustment assembly varies the size of the front opening 42.

A secondary opening 71 with a zipper 70 is located laterally off set from the front opening 42. left eyelets 64 and right eyelets 66 span the front. Both the left eyelets 64 and the right eyelets 66 are laterally offset to opposite sides of the front opening 42.

The first section 14 is integrally fabricated of a laminate 48. The laminate has an inner layer 50 of nylon for comfort, an outer layer 52 of brushed nylon for coupling with a hook and loop fastener, and a middle layer 54 of foam for cushioning and structural strength.

Lastly, the front opening 42 is provided with an adjustment assembly 58. The adjustment assembly 58 has a plurality of left tensioner straps 60 with hook and loop fasteners 61, a plurality of right tensioner straps 62 with hook and loop fasteners 63, a plurality of left eyelets 64, a plurality of right eyelets 66, and a plurality of elastic cords 68. Each elastic cord 68 has a left end attached to an associated left tensioner strap 60 and a right end attached to an associated right tensioner strap 62. Each elastic cord 68 extends from an associated left tensioner strap 60 along the exterior across the front opening 42 then downwardly through an associated right eyelet 66, then along the interior across the front opening, then upwardly through an associated left eyelet 64, then along the exterior and across the front opening, and then attached to the associated right tensioner strap 62. The positioning of the tensioner straps 60 and 62 on the exterior functions to vary a pressure applied by the compression garment to the leg and the foot of the wearer.

Figure 4:
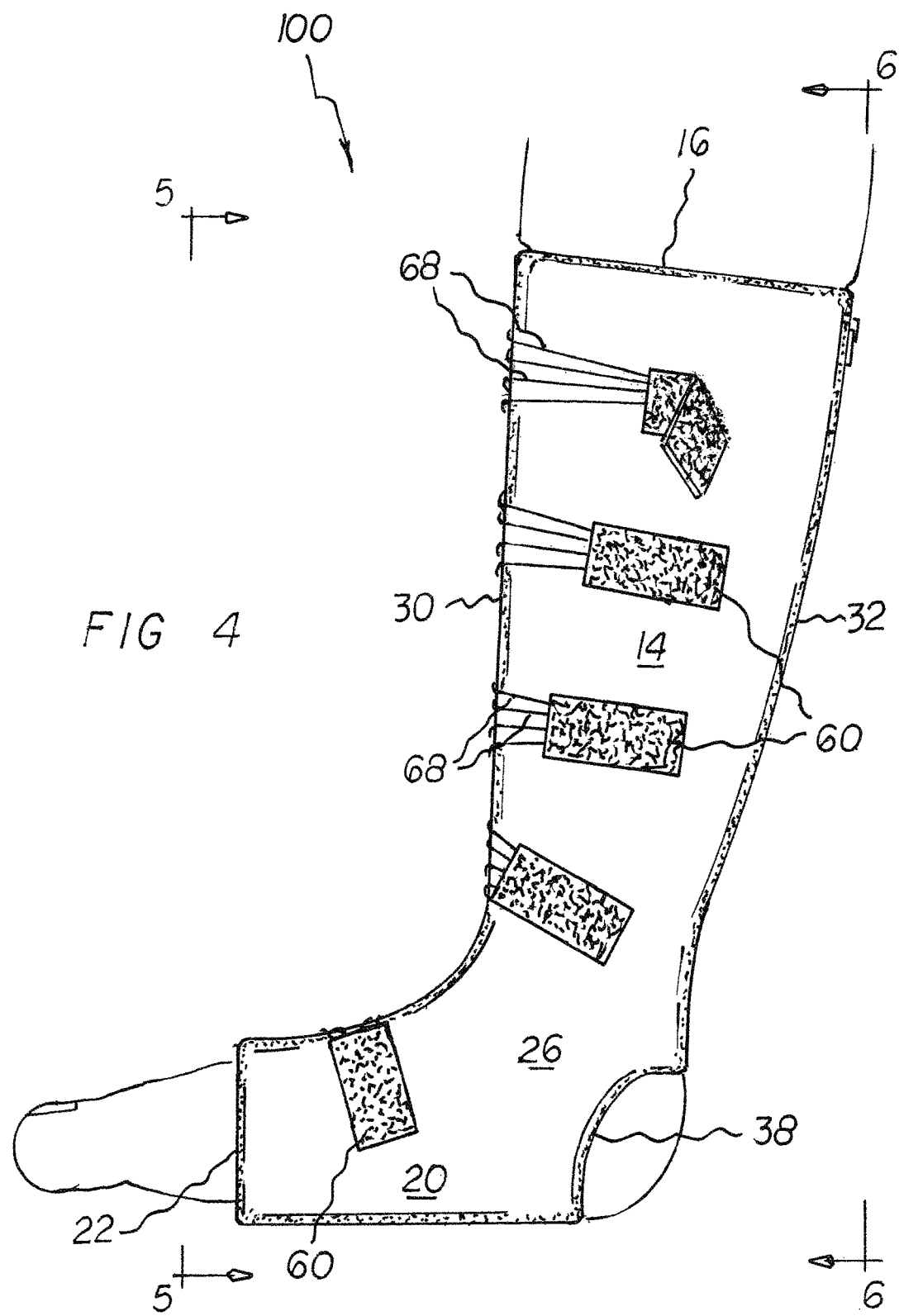
FIG. 4 is a left elevational view of an alternate embodiment of the invention.
Figures 5, 6:
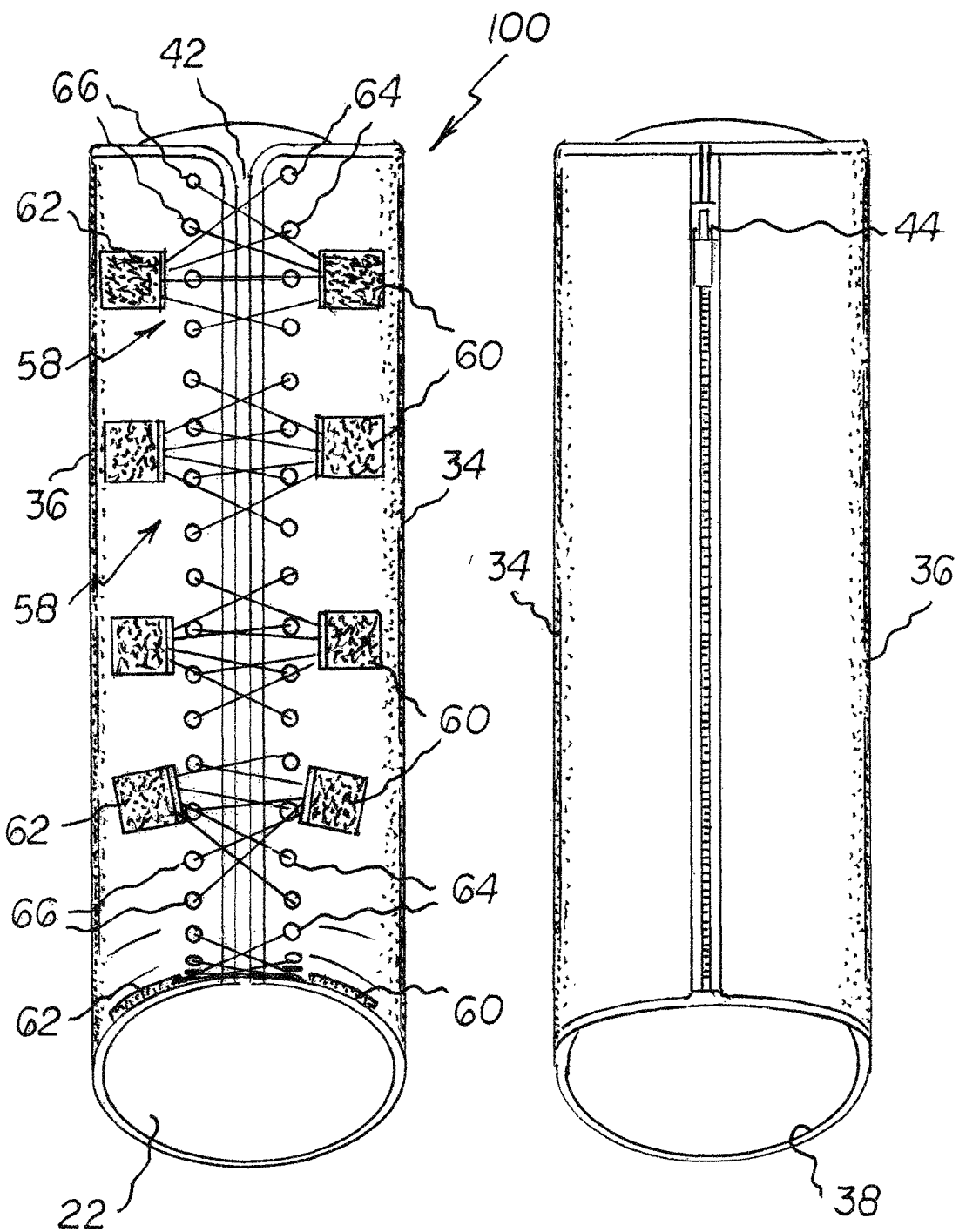
FIG. 5 is a front elevational view taken along line 5-5 of FIG. 4.
FIG. 6 is a rear elevational view taken along line 6-6 of FIG. 4.
Figure 7:
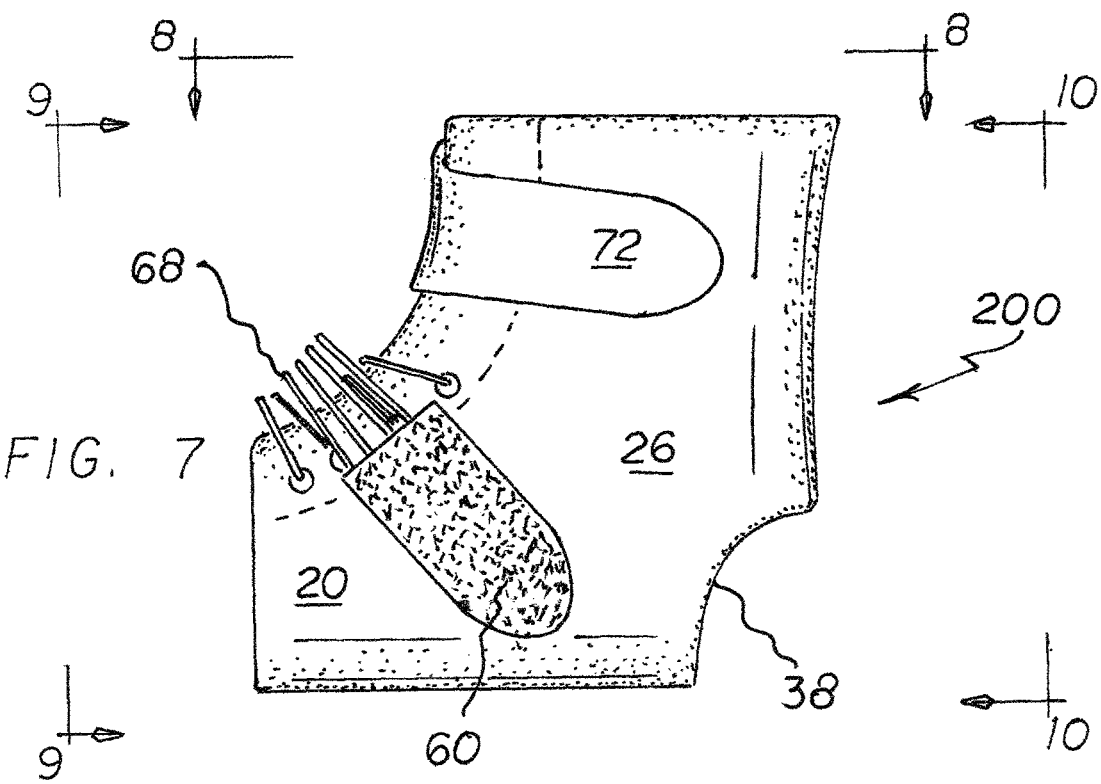
FIG. 7 is a left elevational view of an additional alternate embodiment of the invention.
Figure 8:
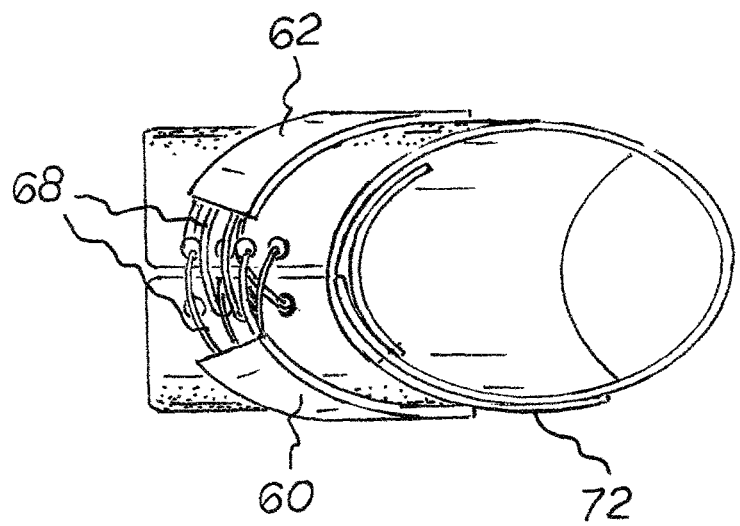
FIG. 8 is a plan view taken along line 8-8 of FIG. 7.
Figure 9:
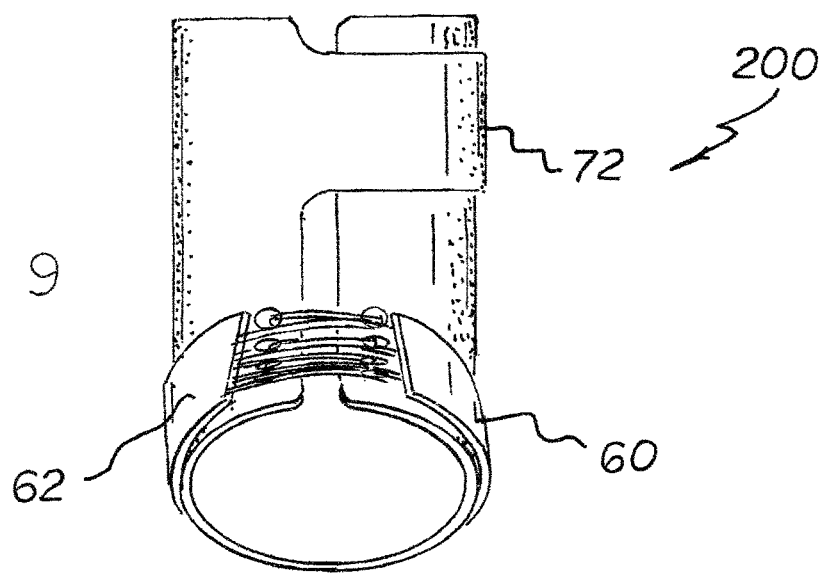
FIG. 9 is a front elevational view taken along line 9-9 of FIG. 7.
Figure 10:
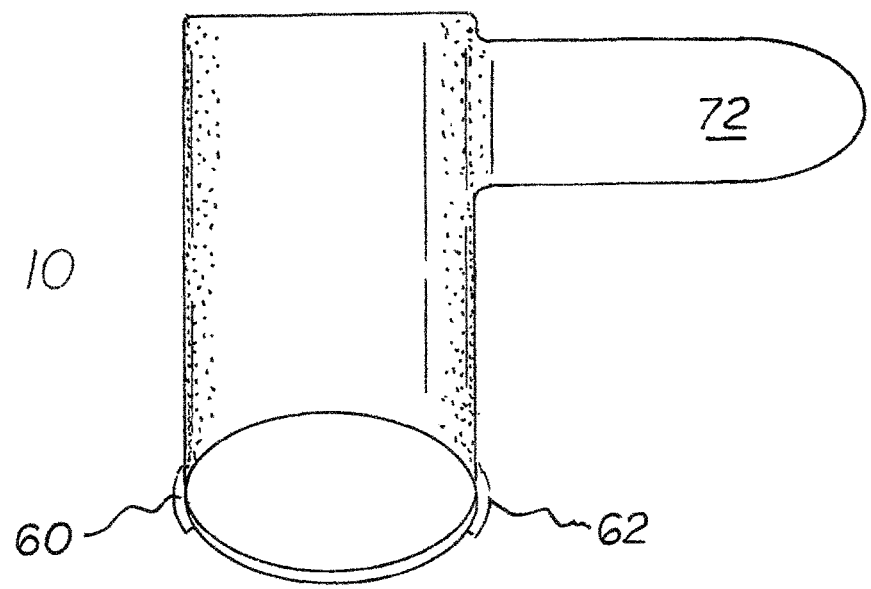
FIG. 10 is a rear elevational view taken along line 10-10 of FIG. 7.

An alternate embodiment 100 of the invention is illustrated in FIGS. 4-6. The preferred embodiment of the compression garment designated by reference numeral 100, is for applying a compressive force to a leg and foot of a wearer and for abating an occurrence of, and guarding against a future progression of, edema and phlebitis and thrombosis.

First provided is an upper section 14 in a generally frustoconical configuration with a generally vertical axis. The upper section encompasses a lower leg of the wearer. The upper section has a bottom and an open top 16.

Next provided is a lower section 20 in a generally frustoconical configuration with a generally horizontal axis. The lower section 20 encompasses a foot of the wearer. The lower section has a top and an open bottom 22.

Next an intermediate section 26 in a generally L-shaped configuration is provided. The intermediate section 26 couples the bottom of the upper section 14 and the top of the lower section 20.

The upper section 14, the lower section 20, and the intermediate section 26 each have a front 30, a back 32, a left side 34, and a right side 36. The compression garment has an interior and an exterior. An open heel 38 is provided in the back of the intermediate section 26 for a heel of the wearer.

A front opening 42 is provided in the front extending from the open top 16 to a location adjacent to the open bottom 22. An adjustment assembly 58 varies the size of the front opening 42.

The upper section 14, the lower section 20, and the intermediate section 26 are integrally fabricated of a laminate 48. The laminate has an inner 50 layer of nylon for comfort, an outer layer 52 of brushed nylon for coupling with a hook and loop fastener, and a middle layer 54 of foam for cushioning and structural strength.

Lastly, the front opening 42 is provided with an adjustment assembly 58. The adjustment assembly 58 has a plurality of left tensioner straps 60 with hook and loop fasteners 61, a plurality of right tensioner straps 62 with hook and loop fasteners 63, a plurality of left eyelets 64, a plurality of right eyelets 66, and a plurality of elastic cords 68. Each elastic cord 68 has a left end attached to an associated left tensioner strap 60 and a right end attached to an associated right tensioner strap 62. Each elastic cord 68 extends from an associated left tensioner strap 60 along the exterior across the front opening 42 then downwardly through an associated right eyelet 66, then along the interior across the front opening, then upwardly through an associated left eyelet 64, then along the exterior and across the front opening, and then attached to the associated right tensioner strap 62. The positioning of the tensioner straps 60 and 62 on the exterior functions to vary a pressure applied by the compression garment to the leg and the foot of the wearer.

FIGS. 7-10 illustrate an additional alternate embodiment of the invention. Such additional alternate embodiment is an anklet compression garment 200. Such anklet compression garment includes a lower section 20 having tensioner straps 60 and 62 and eyelets and cords 68, and such anklet compression garment includes an upper section with a strap 72 having hook and loop fasteners. Such anklet compression garment includes an intermediate section 26.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A compression garment for applying a compressive force to a limb of a user, the compression garment comprising:
   a first section configured to wrap around a lower leg of an individual when secured to the individual and apply a compressive force to the lower leg, the first section having first and second opposed edges extending between a top and a bottom of the first section and defining a first opening in the garment, and third and fourth opposed edges extending between the top and the bottom of the first section defining a second opening in the garment;
   at least three tensioners spaced along the first section between the top and bottom thereof, each of the tensioners having a left side tensioner strap, a right side tensioner strap, and a plurality of elastic cords, each of the elastic cords being threaded through respective eyelets located along the first and second opposed edges and attached at one end to the left side tensioner strap and attached at an opposite end to the right side tensioner strap, the left side tensioner strap and the right side tensioner strap being movable toward and away from each other to bring the first and second opposed edges toward or away from one another to increase or decrease circumferential compression of the lower leg, and wherein the left side tensioner strap and the right side tensioner strap are removably attachable at respective attachment positions to an exterior surface of the first section to secure their relative positions;
   wherein the circumferential compression applied to the lower leg by each of the at least three tensioners is independently adjustable;
   a zipper along the third and fourth opposed edges for releasably connecting the third and fourth opposed edges and closing the second opening; and
   wherein the second opening is located at a position between the first opening and the attachment position of each right side tensioner strap to the first section.

2. The compression garment of claim 1, wherein the first section is frustoconical shaped.

3. The compression garment of claim 1, wherein the zipper extends beyond the bottom of the first section.

4. The compression garment of claim 1, wherein the first section has a laminate construction with an inner layer of nylon material, and an outer layer of brushed nylon material for engagement with hook-and-loop fasteners, and a middle layer of a foam material for cushioning and structural strength.

5. The compression garment of claim 1, wherein the first section has a front and a back, and wherein the first opening and the second opening are both provided in the front of the first section.

6. A compression garment for applying a compressive force to a limb of a user, the compression garment comprising:
   a first section that is frustoconical shaped and configured to wrap around a lower leg of an individual when secured to the individual and apply a compressive force to the lower leg, the first section having first and second opposed edges extending between a top and a bottom of the first section and defining a first opening in the garment, and third and fourth opposed edges extending between the top and the bottom of the first section defining a second opening in the garment;
   at least three tensioners spaced along the first section between the top and bottom thereof, each of the tensioners having a left side tensioner strap, a right side tensioner strap, and a plurality of elastic cords, each of the elastic cords being threaded through respective eyelets located along the first and second opposed edges and attached at one end to the left side tensioner strap and attached at an opposite end to the right side tensioner strap, the left side tensioner strap and the right side tensioner strap being movable toward and away from each other to bring the first and second opposed edges toward or away from one another to increase or decrease circumferential compression of the lower leg, and wherein the left side tensioner strap and the right side tensioner strap are removably attachable at respective attachment positions to an exterior surface of the first section to secure their relative positions;

wherein the circumferential compression applied to the lower leg by each of the at least three tensioners is independently adjustable;

a zipper along the third and fourth opposed edges for releasably connecting the third and fourth opposed edges and closing the second opening, and wherein the zipper extends beyond the bottom of the first section;

wherein the second opening is located at a position between the first opening and the attachment position of each right side tensioner strap to the first section;

wherein the first section has a laminate construction with an inner layer of nylon material, and an outer layer of brushed nylon material for engagement with hook-and-loop fasteners, and a middle layer of a foam material for cushioning and structural strength; and wherein the first section has a front and a back, and wherein the first opening and the second opening are both provided in the front of the first section.

* * * * *